United States Patent [19]

Greenwald et al.

[11] Patent Number: 5,614,549
[45] Date of Patent: Mar. 25, 1997

[54] HIGH MOLECULAR WEIGHT POLYMER-BASED PRODRUGS

[75] Inventors: Richard B. Greenwald, Somerset; Annapurna Pendri, Matawan, both of N.J.

[73] Assignee: Enzon, Inc., Piscataway, N.J.

[21] Appl. No.: 380,873

[22] Filed: Jan. 30, 1995

Related U.S. Application Data

[63] Continuation-in-part of Ser. No. 140,346, Oct. 20, 1993, abandoned, which is a continuation-in-part of Ser. No. 28,743, Mar. 9, 1993, abandoned, which is a continuation-in-part of Ser. No. 934,131, Aug. 21, 1992, abandoned.

[51] Int. Cl.$^6$ ........................ A61K 31/335; C07D 305/14
[52] U.S. Cl. ........................ 514/449; 514/283; 528/421; 546/48; 546/51; 549/510; 549/511
[58] Field of Search ................................ 549/510, 511; 546/48, 51; 514/283, 449; 528/421

[56] References Cited

U.S. PATENT DOCUMENTS

| | | | |
|---|---|---|---|
| 4,191,380 | 7/1978 | Rubenstein et al. | 195/63 |
| 4,680,338 | 7/1987 | Sundoro | 525/54.1 |
| 4,814,470 | 3/1989 | Colin et al. | 514/449 |
| 4,942,184 | 7/1990 | Haugwitz et al. | 514/449 |
| 4,943,579 | 7/1990 | Vishnuvajjala et al. | 514/283 |
| 4,960,790 | 10/1990 | Stella et al. | 514/449 |
| 5,004,758 | 4/1991 | Boehm et al. | 514/283 |
| 5,015,744 | 5/1991 | Holton | 549/510 |
| 5,019,504 | 5/1991 | Christen et al. | 435/123 |
| 5,059,699 | 10/1991 | Kingston et al. | 549/511 |
| 5,136,060 | 8/1992 | Holton | 549/510 |
| 5,157,049 | 10/1992 | Haugwitz et al. | 514/449 |
| 5,227,400 | 7/1993 | Holton et al. | 514/444 |
| 5,229,526 | 7/1993 | Holton | 549/213 |
| 5,272,171 | 12/1993 | Ueda et al. | 514/449 |
| 5,278,324 | 1/1994 | Kingston et al. | 549/510 |
| 5,342,947 | 8/1994 | Lackey et al. | 546/41 |
| 5,352,805 | 10/1994 | Kingston et al. | 549/510 |
| 5,362,831 | 11/1994 | Mongelli et al. | 526/304 |
| 5,498,729 | 3/1996 | Domb | 548/500 |

FOREIGN PATENT DOCUMENTS

| | | |
|---|---|---|
| 0524093 | 1/1993 | European Pat. Off. |
| 9324476 | 12/1993 | WIPO. |

OTHER PUBLICATIONS

Bioconjugate Chemistry Sep./Oct. 1992 vol. 3, No. 5; 351–362, Maeda, Hiroshi et al.
Journal of Bioactive and Compatible Polymers vol. 10– Jan. 1995, 51–66; Ohya, Yuichi et al.
Polymer Bulliten 18, 487–493 (1987) Gehrardt et al.
J. of Controlled Release 10, (1989) 145–154 Veronese, F et al.
Cancer Chemother Pharmacol (1992) 31 255–257 Waud, W. et al.
Biotechnology and Applied Biochemistry 9, 258–268 (1987) Buckn, A. et al.
J. Med. Chem, (1991), 34, 992–998, Francoise Gueritte–Voegelein, et al.
J. Org. Chem, (1986), 51, 797–802, Neil F. Magri, et al.
Journal of Medicinal Chemistry, (1973), vol. 16, No. 5, 573–574, Ben–Zion Weiner, et al.
Nature, vol. 364, 29 Jul. 1993, K.C. Nicolaou, et al.
Tetrahedron Letters, vol. 33, No. 36, pp. 5185–5188, 1992, A. Commercon, et al.
Proc. Int. Symp. Control. Release Bioact. Mater., 21 (1994), #1368, Yuichi Ohya, et al.
Cancer Treatment Reviews (1990), 17, 127–131, Terrence W. Doyle, et al.
Bioorganic & Medicinal Chemistry Letters, Vo. 4, No. 18, pp. 2223–2228 (1994) Shu–Hui Chen, et al.
Journal of Pharmaceutical Sciences, vol. 83, No. 4, Apr. 1994, Tetsuji Yamaoka, et al.
Bioorganic & Medicinal Chemistry Letters, vol. 4, No. 20, pp. 2465–2470, 1994, Richard B. Greenwald, et al.
Clinical Pharmacy, vol. 8, Apr. 1989, pp. 274–293, Ronald A. Fleming, et al.
Oncology, Dec. 1992, pp. 17–23, Michael J. Hawkins, et al.
Drug Design and Discovery, 1992, vol. 9, pp. 93–105, Tatsuro Ouchi, et al.
Eur. Polym. J., vol. 19, No. 12, pp. 1177–1183, S. Zalipsky, et al.
Angew. Chem. Int. Ed. Engl., 1994, 33, No. 1516, pp. 1583–1587, Kyriacos Costa Nicolaou, et al.
J. Med. Chem., 1992, 35, 145–151, Abraham E. Mathew, et al.
J. Med. Chem., 1981, 24, 622–625, R. Cecchi, et al.
"Novel, Water–Soluble Phosphate Derivatives of 2'–Ethoxycarbonyl Paclitaxel . . . ", Bioorganic & Medicinal Chemistry Letters, vol. 5, No. 3, pp. 247–252 (1995).
"Synthesis and Antitumor Evaluation of 2'–Oxycarbonyl Paclitaxel" Bioorganic & Medicinal Chemistry Letters, vol. 4, No. 15, pp. 1861–1864 (1994).

*Primary Examiner*—Ba K. Trinh
*Attorney, Agent, or Firm*—Michael N. Mercanti

[57] ABSTRACT

Water-soluble prodrugs of the formula:

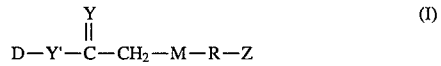

wherein:
D is a biologically active nucleophile;
M is X or Q;
x is an electron withdrawing group;
Q is a moiety containing a free electron pair positioned five or six atoms from Y';
Y and Y' are oxygen or sulfur;
R is a polyalkylene oxide; and
Z is OH, $C_{1-4}$ alkyl moieties or

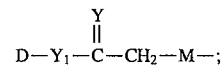

are disclosed.

10 Claims, No Drawings

HIGH MOLECULAR WEIGHT POLYMER-BASED PRODRUGS

RELATED APPLICATIONS

This application is a continuation-in-part of U.S. patent application Ser. No. 08/140,346 filed Oct. 20, 1993 now abandoned, which, in turn, is a continuation-in-part of U.S. patent application Ser. No. 08/028,743 filed Mar. 9, 1993, now abandoned which in turn, is a continuation-in-part of U.S. patent application Ser. No. 07/934,131, filed Aug. 21, 1992 now abandoned.

TECHNICAL FIELD

The present invention relates to water soluble prodrugs. In particular, the invention relates to the use of relatively high molecular weight non-antigenic polymers to prepare prodrugs.

BACKGROUND OF THE INVENTION

Over the years, several methods of administering biologically-effective materials to mammals have been proposed. Many medicinal agents are available as water-soluble salts and can be included in pharmaceutical formulations relatively easily. Problems arise when the desired medicinal is either insoluble in aqueous fluids or is rapidly degraded in vivo. Alkaloids are often especially difficult to solubilize.

For example, several methods have been suggested to overcome the problems associated with administering paclitaxel, (also known as Taxol®, Bristol-Myers Squibb Co. NY, N.Y.), which is insoluble in water. Currently, taxol is administrated in physical admixture with a non-aqueous vehicle, cremophor-EL. This formulation, however, has several drawbacks. Hypersensitivity reactions have been associated with the vehicle and intravenous administration of the agent with this vehicle is also slow and causes discomfort to the patient.

Several methods have been suggested to enhance the aqueous solubility of taxol. See, for example, PCT WO 93/24476, U.S. Pat. No. 5,362,831, and Nicolaou, et al. *Angew. Chem. Int. Ed. Engl.*(1994) 33, No. 15/16, pages 1583–1587. Preparing water-soluble prodrug versions has also been explored.

Prodrugs include chemical derivatives of a biologically-active parent compound which, upon administration, will eventually liberate the active parent compound in vivo. Use of prodrugs allows the artisan to modify the onset and/or duration of action in vivo. In addition, the use of prodrugs can modify the transportation, distribution or solubility of a drug in the body. Furthermore, prodrugs may reduce the toxicity and/or otherwise overcome difficulties encountered when administering pharmaceutical preparations.

A typical example in the preparation of prodrugs can involve conversion of alcohols or thioalcohols to either organic phosphates or esters. *Remington's Pharmaceutical Sciences,* 16th Ed., A. Osol, Ed. (1980).

Prodrugs are often biologically inert or substantially inactive forms of the parent or active compound. The rate of release of the active drug is influenced by several factors including the rate of hydrolysis of the converted ester or other functionality.

Recently, polyethylene glycol and related polyalkylene oxides have been suggested as possible adjuncts for the preparation of taxol prodrugs. See PCT WO93/24476 supra, for example. PEG has also been conjugated to proteins, peptides and enzymes to increase aqueous solubility and circulating life in vivo as well as reduce antigenicity. See, for example, U.S. Pat. Nos. 5,298,643 and 5,321,095, both to Greenwald, et al. These latter two references disclose, inter alia, biologically-active conjugates having substantially hydrolysis-resistant bonds (linkages) between a polyalkylene oxide and the target moiety. Thus, long-lasting conjugates rather than prodrugs per se were prepared. In most situations, the average molecular weight of the polymer included in the conjugate was preferably about 5,000 daltons.

PCT WO 93/24476 discloses using an ester linkage to covalently bind taxol to water-soluble polyethylene glycols and provide a prodrug. Applicants, however, have discovered that the ester linkages described therein provide $t_{1/2}$ for hydrolysis of greater than four days in aqueous environments. Thus, most of the conjugate is eliminated prior to hydrolysis being achieved in vivo. It would be preferable to provide an ester linkage which allows more rapid hydrolysis of the polymer-drug linkage in vivo so as to generate the parent drug compound more rapidly.

It has also been surprisingly found that when only one or two polymers of less than 10,000 molecular weight are conjugated to alkaloids and/or organic compounds, the resulting conjugates are rapidly eliminated in vivo. In fact, such conjugates are so rapidly cleared from the body that even if a hydrolysis-prone ester linkage is used, not enough of the parent molecule is regenerated in vivo to make the PAO-drug conjugate worthwhile as a prodrug.

Yamaoka, et al. *J. Pharmaceutical Sciences,* Vol. 83, No. 4, April 1994, pages 601–606, disclose that the half-life of unmodified PEG in circulation of mice after IV administration extended from 18 minutes to one day when molecular weight was increased from 6,000 to 190,000. Yamaoka, et al., however, failed to consider the effect linking the polymer to a drug would have on the drug. Also, Yamaoka, et al. failed to consider that aqueous solutions of higher molecular weight polymers are quite viscous and difficult to dispense through the narrow-bore devices used to administer pharmaceutical preparations.

In summary, previous prodrugs based on conjugates of parent drug compounds with water soluble polymers have not been successful due to a combination of excessively slow hydrolysis of the polymer from the parent drug and excessively rapid clearance of the prodrug from the body.

SUMMARY OF THE INVENTION

The present invention addresses the shortcomings described above. In one aspect of the invention, compositions of formula (I) are provided:

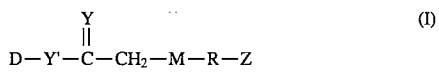

wherein:

D is a biologically active nucleophile;

M is X or Q;

X is an electron withdrawing group;

Q is a moiety containing a free electron pair positioned five or six atoms from Y';

Y and Y' are independently O or S;

R is a polyalkylene oxide; and

Z is one of OH, a $C_{1-4}$ alkyl moiety or

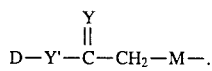

In some preferred embodiments of the invention, compositions of formula (II) and (III) are provided:

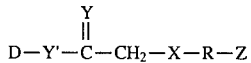 (II)

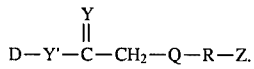 (III)

The prodrugs include a water-soluble polyalkylene oxide polymer (designated R herein). In particular, R is preferably a polyethylene glycol and has a molecular weight of at least about 20,000.

The prodrug compositions of the present invention can include one or two active compounds attached to the water-soluble polymer each via a hydrolyzable linkage such as a suitably activated ester linkage. Thus, mono- and bispolymer-based prodrugs are contemplated.

In certain preferred aspects of the invention, the active or parent compound (designated D herein) attached to the polymer is a taxoid such as taxol, taxane, or taxotere. In other aspects of the invention, the active or parent compound is camptothecin, etoposide or podophyllotoxin. In still further embodiments, non-oncolytic agents such as anti-inflammatory agents, including steroidal compounds, as well as therapeutic low molecular weight peptides such as peptidoglycans are also contemplated.

One of the chief advantages of the compounds of the present invention is that the prodrugs achieve a proper balance between the rate of linkage hydrolysis and the rate of clearance of prodrug from the body. The linkage between the polymer and the parent compound, also referred to herein as a biologically-active nucleophile, hydrolyzes at a rate which allows a sufficient amount of the parent molecule to be released in vivo before clearance of the prodrug from the plasma or body.

Methods of making and using the compositions described herein are also provided.

DETAILED DESCRIPTION OF THE INVENTION

A. THE PRODRUGS

The prodrug compositions of the present invention contain hydrolyzable linkages between the polymer portion and biologically active nucleophile. These linkages are preferably ester linkages designed to hydrolyze at a rate which generates sufficient amounts of the biologically active parent compound in a suitable time. The term "sufficient amounts" for purposes of the present invention shall mean an amount which achieves a therapeutic effect.

In one aspect of the invention, the prodrugs of the invention are the formula (I), as set forth below:

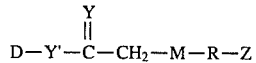 (I)

wherein:
  D is a biologically active nucleophile;
  M is X or Q;
  X is an electron withdrawing group;
  Q is a moiety containing a free electron pair positioned five or six atoms from Y';

Y and Y' are independently O or S;
R is a polyalkylene oxide; and
Z is one of OH, a $C_{1-4}$ alkyl moiety or

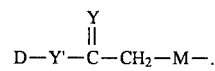

Within Formula (I), Y and Y' are preferably oxygen. In those aspects where M is X as shown below:

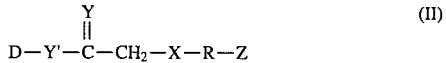 (II)

X is an electron withdrawing group which gives a substituted acetic acid with a pKa of less than about 4.0 upon hydrolysis of the prodrug ester. Thus, X can be one of O, —N(L)—C(O)—, —C(O)—N(L), C(O), N(L) or $SO_2$;

wherein L is selected from the group consisting of H, $C_{1-8}$ alkyls, cycloalkyls, aryls and aralkyls. Suitable alkyls include straight or branched alkyls, preferably methyl. Suitable aryls include phenyl or substituted phenyls; suitable aralkyls include benzyls. X is preferably one of O, —N(H)C(O)—or C(O)N(H)—.

The moieties selected for X promote relatively rapid hydrolysis because of the low pKa of the resulting substituted acetic acid.

In another embodiment of the invention, compositions of Formula (III) are provided:

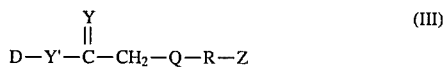 (III)

wherein:
  D, Y',Y, R and Z are the same as that set forth above in Formula (I) and R is preferably attached to Q via a heteroatom, preferably O. Q is a moiety containing a free electron pair positioned three to six atoms from Y' as shown below in FIG. (III')

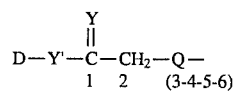

In a preferred embodiment, the free electron pair is five atoms from Y'. Q can be selected from the non-limiting list of $C_{2-4}$ alkyls or cycloalkyls, aryls or aralkyl groups substituted with a member of the group consisting of OH, SH and NH(L), wherein L is a $C_{1-8}$ alkyl, cycloalkyl, aryl or aralkyl. The free electron pair can be anywhere along the Q moiety as long as the defined spacing between the free electron pair and Y' is maintained.

Some particularly preferred moieties for Q include:
  —$CH_2$—C(O)—N(H)—, and ortho-substituted phenyl groups such as

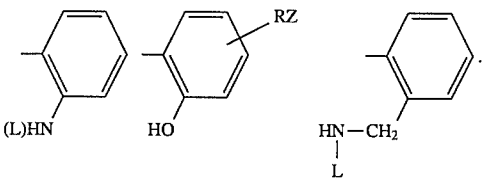

In these embodiments, the R-Z portion can be attached via L, a hetero atom (O,N,S) or aryl group. Thus, Q, in formula (III), assists hydrolysis of the prodrug ester by anchimeric assistance because the free electron pair moiety generates a three to six, preferably five-membered ring by-product upon hydrolysis of the ester.

In another alternative aspect of the invention, the methylene portion of Formula III is not included, as shown below in (III"):

 (III")

In this aspect, it is understood that the defined spacing between the free electron pair and Y' is maintained.

In both Formulas (II) and (III), Z represents the terminal portion of the water soluble polyalkylene oxide polymer. Suitable polymer terminal groups include hydroxyl, $CH_3$ or a $C_{1-4}$ alkyl when the prodrugs include a single biologically active nucleophile. On the other hand, the prodrugs of Formula (I) can also include disubstituted polymers. Thus, in the case of Formula (I), Z is a moiety of Formula (IV):

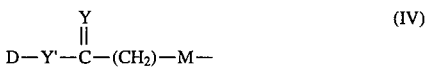 (IV)

wherein each of the variables is the same as that set forth for Formula (I) above.

In the particular case of Formula (II), Z is a moiety of Formula (V):

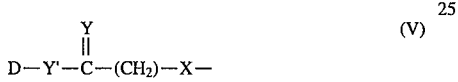 (V)

and, in the case of Formula (Ill), Z is a moiety of Formula (VI):

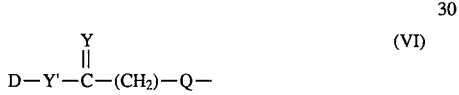 (VI)

wherein each of the variables is the same as that set forth for Formula (II) above.

B. SUBSTANTIALLY NONANTIGENIC POLYMERS

The prodrug compositions of the present invention include a water-soluble polymer, R. Suitable examples of such polymers include polyalkylene oxides such as polyethylene glycols which are also preferably substantially nonantigenic.

In particular, polyethylene glycols (PEG's), mono-activated, $C_{1-4}$ alkyl-terminated PAO's such as monomethyl-terminated polyethylene glycols (mPEG's) are preferred when mono- substituted polymers are desired; bis-activated polyethylene oxides are preferred when disubstituted prodrugs are desired. In order to provide the desired hydrolyzable linkage, mono- or di-acid activated polymers such as PEG acids or PEG diacids are used. Suitable PAO acids can be synthesized by converting mPEG-OH to an ethyl ester. See also Gehrhardt, H., et al. Polymer Bulletin 18: 487 (1987) and Veronese, F. M., et al., J. Controlled Release 10; 145 (1989). The disclosures of each of the foregoing are incorporated by reference herein.

Although PAO's and PEG's can vary substantially in molecular weight, polymers having molecular weight ranges of at least 20,000 are preferred. Polymers ranging from about 20,000 to about 80,000 are usually selected for the purposes of the present invention. Molecular weights of from about 25,000 to about 45,000 are preferred and 30,000 to about 42,000 are particularly preferred. The molecular weight of the polymer selected for inclusion in the prodrug must be sufficient so as to provide sufficient circulation of the prodrug during hydrolysis of the linker.

The polymeric substances included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers maintained.

Particularly preferred polymers useful in forming the prodrugs include polymers of the formula (VII)

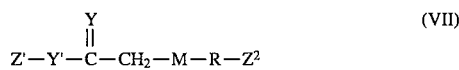 (VII)

wherein:

M is X or Q;

Z' is OH or a $C_{1-4}$ alkyl;

$Z^2$ is OH, a $C_{1-4}$ alkyl or

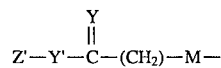

wherein each of M, Q, X, R, Y, and Y' are the same as that set forth above and at least one of Z' and $Z^2$ is OH. Y and Y' are preferably O, and R has a molecular weight of about 20,000 or greater.

The following PEG acids and PEG diacids are especially preferred:

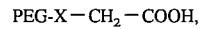

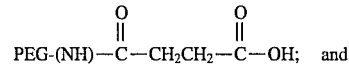

As an alternative to PAO-based polymers, effectively non-antigenic materials such as dextran, polyvinyl alcohols, carbohydrate-based polymers and the like can be used if the same type of ester activation is employed as described herein for PAO's such as PEG, i.e. conversion of alcohol to a 2-alkoxy acid. Those of ordinary skill in the art will realize that the foregoing list is merely illustrative and that all polymeric materials having the qualities described herein are contemplated. For purposes of the present invention, "effectively non-antigenic" means all polymeric materials understood in the art as being nontoxic and not eliciting an appreciable immune response in mammals.

C. PRODRUG CANDIDATES

1. Taxoids and Taxoid Derivatives

One class of compounds included in the prodrug compositions of the present invention is taxoids. For purposes of the present invention, the term "taxoid" includes all compounds within the taxane family of terpenes. Thus, taxol (paclitaxel), 3'-substituted tert-butoxy-carbonyl-amine derivatives (taxoteres) and the like as well as other analogs available from, for example, PHYTOPharmaceuticals, Inc. San Carlos, Calif. and/or Signa Chemical of St. Louis, Mo. are within the scope of the present invention. Representative taxoids are shown below.

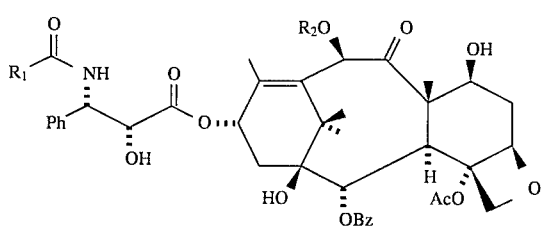

Taxol: $R_1 = C_6H_5$: $R_2 = CH_3CO$
Taxotere: $R_1 = (CH_3)_3CO$: $R_2 = H$

These compounds have been found to be effective anticancer agents. Numerous studies indicate that the agents have activity against several malignancies. To date, their use has been severely limited by, among other things, their short supply, poor water solubility and immunogenicity. One particularly beneficial class of taxoids are the 7-aryl-carbamates, represented below by Formula (VIII):

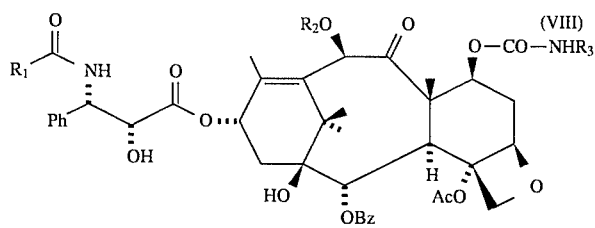

wherein, $R_1$ is $C_6H_5$ or $(CH_3)_3$ CO;

$R_2$ is $CH_3$ CO or H;

$R_3$ is aryl, aralkyl, or heteroaryl.

Within this aspect, one particularly preferred taxoid includes $R_3$ as phenyl.

Although the examples describe inter alia taxol for illustrative purposes, it is to be understood that the methods described herein are suitable for all taxoids and related molecules. The only limitation on this provision is that the selected taxoid must be capable of undergoing 2' position modifications described herein. Taxol, however, is a preferred taxoid.

Formation of the taxoid-based prodrugs of the invention is set forth below in section D and in the Examples.

Generally, a taxoid having the 2' position available for substitution is reacted with a suitably activated polymer such as a PEG acid under conditions sufficient to cause the formation of a 2' ester linkage between the two substituents. As illustrative examples, taxol and taxotere are shown below:

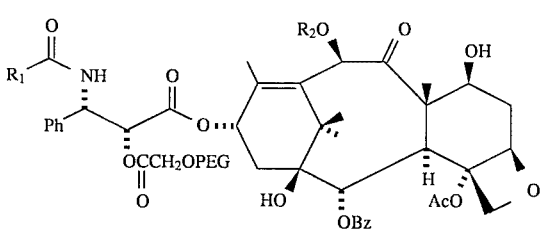

ProTaxol: $R_1 = C_6H_5$: $R_2 = CH_3CO$
ProTaxotere: $R_1 = (CH_3)_3CO$: $R_2 = H$ The corresponding diester can be prepared by reacting at least about 2 equivalents of taxoid per polymer diacid.

2. Camptothecin and Related Topoisomerase I Inhibitors

Camptothecin is a water-insoluble cytotoxic alkaloid produced by camptoteca accuninata trees indigenous to China and nothapodytes foetida trees indigenous to India. Camptothecin and related compounds are also candidates for conversion to the prodrugs of the present invention. See, for example, U.S. Pat. No. 5,004,758 and Hawkins, Oncology, December 1992, pages 17–23. Camptothecin and related analogues have the structure:

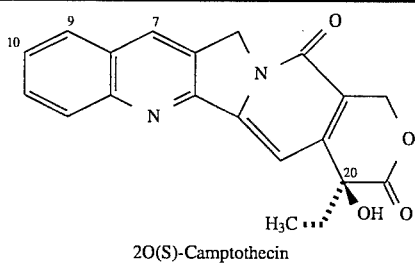

20(S)-Camptothecin

| Camptothecin analogues | Position | | |
|---|---|---|---|
| | 7 | 9 | 10 |
| Topotecan | H | $CH_2N(CH_3)_2$ | OH |
| CPT-11 | $-CH_2-CH_3$ | H | ![piperidine-piperidine-carbamate] |

Formation of the camptothecin prodrug is accomplished by reacting a suitably activated polymer with the camptothecin derivative under conditions sufficient to effect attachment of an ester linkage to the OH situated in the 20 position. Camptothecin diesters are similarly prepared by reacting at least about 2 equivalents of the camptothecin with a suitably prepared PAO diacid. Details concerning the reaction conditions are provided in Section D, below and in the Examples.

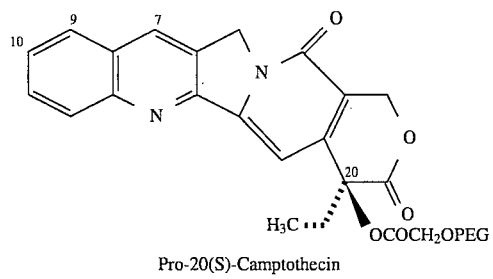

Pro-20(S)-Camptothecin

| Pro-Camptothecin analogues | Position | | |
|---|---|---|---|
| | 7 | 9 | 10 |
| Pro-Topotecan | H | CH$_2$N(CH$_3$)$_2$ | OH |
| Pro-CPT-11 | —CH$_2$—CH$_3$ | H | ![piperidine-piperidine carbamate] |

3. Additional Bioloqically-Active Nucleophiles

In addition to the foregoing molecules, the prodrug formulations of the present invention can be prepared using many other compounds. For example, biologically-active compounds such as etoposide (VePesid™, Bristol Myers, New York, N.Y.), podophyllotoxin and related compounds can be included. The prodrug ester is formed at the C$_4'$ hydroxy for etoposide and at the C$_4$ hydroxy for podophyllotoxin. The parent compounds selected for prodrug forms need not be substantially water-insoluble, although the polymer-based prodrugs of the present invention are especially well suited for delivering such water-insoluble compounds. Other useful parent compounds include certain low molecular weight biologically active proteins, enzymes and peptides, including peptido glycans, as well as other anti-tumor agents, cardiovascular agents, anti-neoplastics, anti-infectives, anti-fungals, anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like are also contemplated.

The foregoing is illustrative of the biologically active nucleophiles which are suitable for the prodrugs of the present invention. It is to be understood that those biologically active materials not specifically mentioned but having suitable ester-forming groups are also intended and are within the scope of the present invention.

The only limitation on the types of molecules suitable for inclusion herein is that there is at least one position on which the hydrolyzable linkage can be attached, so that after prodrug administration, the prodrug can regenerate sufficient quantities of the parent compound in vivo.

D. SYNTHESIS OF PRODRUGS

Synthesis of specific prodrugs is set forth in the Examples. Generally, however, the prodrugs are prepared by 1) providing an activated polymer, such as a PEG-acid and a parent compound having a position thereon which will allow a hydrolyzable linkage to form, 2) reacting the two substituents in an inert solvent such as methylene chloride, chloroform or DMF in the presence of a coupling reagent such as 1,3-diisopropylcarbodiimide and a base such as dimethylaminopyridine at a temperature from 0° C. to 22° C. (room temperature).

E. METHODS OF TREATMENT

Another aspect of the present invention provides methods of treatment for various medical conditions in mammals. The methods include administering to the mammal, an effective amount of a prodrug, such as a taxol 2'-PEG ester, which has been prepared as described herein The compositions are useful for, among other things, treating neoplastic disease, reducing tumor burden, preventing metastasis of neoplasms and preventing recurrences of tumor/neoplastic growths.

The amount of the prodrug administered will depend upon the parent molecule included therein. Generally, the amount of prodrug used in the treatment methods is that amount which effectively achieves the desired therapeutic result in mammals. Naturally, the dosages of the various prodrug compounds will vary somewhat depending upon the parent compound, rate of in vivo hydrolysis, molecular weight of the polymer, etc. In general, however, prodrug taxoids are administered in amounts ranging from about 5 to about 500 mg/m$^2$ per day, based the amount of the taxoid moiety. Camptothecin, etoposide and podophyllotoxin prodrugs are also administered in amounts ranging from about 5 to about 500 mg/m$^2$ per day. The range set forth above is illustrative and those skilled in the art will determine the optimal dosing of the prodrug selected based on clinical experience and the treatment indication.

The prodrugs of the present invention can be included in one or more suitable pharmaceutical compositions for administration to mammals. The pharmaceutical compositions may be in the form of a solution, suspension, tablet, capsule or the like, prepared according to methods well known in the art. It is also contemplated that administration of such compositions may be by the oral and/or parenteral routes depending upon the needs of the artisan.

F. EXAMPLES

The following examples serve to provide further appreciation of the invention but are not meant in any way to restrict the effective scope of the invention.

EXAMPLE 1

PREPARATION OF BIS(TAXOL-2'-ESTER) OF PEG 40,000 DIACID

A. PEG 40,000 DICARBOXYLIC ACID PREPARATION

A solution of 50 grams (1.3 mmoles) of PEG-diol (40,000) in 750 ml of toluene was azeotroped with the removal of 150 ml of distillate. The reaction mixture was then cooled to 30° C., followed by the addition of 4 ml (4.0 mmoles) of a 1.0 molar solution potassium t-butoxide in t-butanol. The resulting mixture was stirred for 1 hour at room temperature, followed by the addition of 1.6 ml (14 mmoles) ethyl bromoacetate. The resulting mixture was heated to reflux, followed by removal of the heat and stirring for 18 hours at room temperature. The reaction mixture was filtered through celite and the solvent removed by rotary evaporator. The residue was recrystallized from methylene chloride/ethyl ether to yield 45.2 grams (86%) yield of PEG (40,000) dicarboxylic acid diethyl ester.

A solution of 20.0 grams (0.5 mmol) of PEG (40,000) dicarboxylic acid ethyl ester, in 1N NaOH (100 ml) was stirred at room temperature for 4 hours. The solution, cooled in an ice bath, was brought to pH 3.0 with 2N HCl and extracted three times with $CH_2Cl_2$. The pooled extracts were washed with $H_2O$, concentrated to 15 ml and the solution was added to ethyl ether (200 ml) under stirring. The precipitate was filtered, washed with ether, dried and crystallized from methylene chloride/ether to yield 16.9 grams (84%) of product.

$C^{13}$ NMR assignments: C=O, 170.9 ppm.

B. BIS(TAXOL-2'-ESTER) OF PEG 40,000 DIACID

The PEG 40,000 diacid from step A was azeotroped in toluene prior to use. The PEG 40,000 diacid (3 grams, 0.125 mmol) was dissolved in 20 ml of anhydrous methylene chloride at room temperature before being treated with 1,3-diisopropyl carbodiimide (52.2 µl, 0.342 mmol), 4-dimethylamino pyridine (64.0 mg, 0.523 mmol) and taxol (291.5 mg, 0.342 mmol) at 0° C. The reaction solution was warmed to room temperature after 30 minutes and kept at that temperature for 16 hours. The reaction solution was then washed with 0.1N HCl, dried and evaporated to yield a white solid which was crystallized from isopropanol to yield 2.56 grams, 91.7%.

EXAMPLE 2

PREPARATION OF 20-CAMPTOTHECIN PEG 40,000 DIESTER

PEG 40,000 diacid prepared in accordance with Example 1 A, was azeotroped in toluene prior to use. The PEG 40,000 diacid (5 grams, 0.125 mmol), was dissolved in 40 ml of anhydrous methylene chloride at room temperature. This solution was treated with 1,3-diisopropyl carbodiimide (53.4 µl 0.350 mmol), 4-dimethylamino pyridine (42.8 mg, 0.350 mmol) and (S)-(+)-camptothecin (121.57 mg, 0.350 mmol) at 0° C. The reaction solution as warmed to room temperature after 30 minutes and kept at that temperature for 16 hours. The reaction solution was then washed with 0.1N HCl, dried and evaporated to yield a solid which was purified by chromatography (silica gel, $MeOH/CH_2CH_2$) The purified material was then crystallized from $CH_2Cl_2$/ether to yield 3.36 grams, 66%.

EXAMPLE 3

PREPARATION OF 20-CAMPTOTHECIN PEG 5,000 ESTER

A. PEG 5,000 CARBOXYLIC ACID PREPARATION

The procedure of Example 1 A was repeated except that m-PEG-OH 5,000 was used instead of the PEG diol.

B. 20-CAMPTOTHECIN PEG 5,000 ESTER PREPARATION

The PEG 5,000 acid was azeotroped in toluene prior to use. The PEG 5,000 acid (400 mg, 0.079 mmol) was dissolved in 10 ml of anhydrous methylene chloride at room temperature before being treated with 1,3-diisopropyl carbodiimide (18.1 µl 0.119 mmol), 4-dimethylamino pyridine (14.5 mg, 0.119 mmol) and (S)-(+)-camptothecin (41.32 mg, 0.119 mmol) at 0° C. The reaction solution was warmed to room temperature over 30 minutes and kept at that temperature for 16 hours. The reaction solution was then washed with 0.1N HCl, dried and evaporated to yield an off-white solid which was purified by chromatography (silica gel, $MeOH/CH_2Cl_2$). The purified material was crystallized from $CH_2Cl_2$/ether.

EXAMPLE 4

TAXOL 2'-PEG 5,000 MONOESTER

A. PEG 5,000 CARBOXYLIC ACID PREPARATION

The procedure of Example 1 A was repeated except that m-PEG-OH 5,000 was used instead of the PEG diol.

B. TAXOL-2'PEG 5,000 MONOESTER PREPARATION

PEG 5,000 acid was azeotroped before use. The PEG 5,000 acid (625 mg, 0.125 mmol) was dissolved in 20 ml of anhydrous methylene chloride at room temperature. The above solution was treated with 1,3-diisopropylcarbodiimide (26 µl, 0.17 mmol), 4-dimethylaminopyridine (32 mg, 0.26 mmol) and taxol (146 mg, 0.17 mmol) at 0° C. The reaction solution was warmed to room temperature after 30 minutes and kept at that temperature for 16 hours. The reaction mixture was then washed with 0.1N HCl, dried and evaporated to yield a white solid which was crystallized from 2-propanol to yield 585 mg (80% yield) of pure product.

EXAMPLE 5

PREPARATION OF 2'-PEG 42,000-TAXOL MONOESTER

A. PEG 42,000 CARBOXYLIC ACID PREPARATION

A solution of 5 grams (0.12 mmol) of MPEG-OH (42,000) in 75 ml of toluene was azeotroped with the removal of 15 ml of distillate. The reaction mixture was then cooled to 30° C., followed by the addition of 0.18 ml (0.18 mmol) of a 1.0 molar solution potassium t-butoxide in t-butanol. The resulting mixture was stirred for 1 hour at room temperature, followed by the addition of 0.13 ml (1.2 mmoles) ethyl bromoacetate. The resulting cloudy mixture was heated to reflux, followed by removal of the heat, and stirring for 18 hours at room temperature. The reaction mixture was filtered through celite and the solvent removed by rotary evaporator. The residue was recrystallized from methylene chloride/ether to yield 4.1 grams (82%) of ethyl ester.

A solution of 4 grams (0.95 mmol) of MPEG (42,000) carboxylic acid ethyl ester, in 1N NaOH (50 ml) was stirred at room temperature for 4 hours. The solution, cooled in an ice bath, was brought to pH 3.0 was 2N HCl and extracted three times with methylene chloride. The pooled extracts were washed with water, concentrating to 15 ml and the solution added to ethyl ether (20 ml) under stirring. The precipitate was filtered, washed with ether, dried and crystallized from 2-propanol to yield 3.7 grams (90%) of MPEG 42,000 acid. $^{13}$C NMR assignment: O$\underline{C}$H3, 58.3 ppm; $\underline{C}$=o, 170.6 ppm.

B. TAXOL-2'-ESTER OF PEG 42,000 MONOESTER

The procedure of Example 4B was repeated except that the PEG 42,000 carboxylic acid of Example 5A was used instead of the 5,000 MW PEG.

EXAMPLE 6

TAXOL 7-PHENYLCARBAMATE

A. N-Hydroxysuccinimidyl methoxyacetate (MAc-NHS)

A suspension containing 2.53 grams (0.022 mmol) of N-hydroxysuccinimide and 2.17 grams (0.02 mmol) methoxyacetyl chloride in 10 milliliters of methylene chloride was prepared and combined with 2.84 grams (0.022 mmol) of diisopropylethylamine in 15 milliliters of methylene chloride over a period of 30 minutes. After stirring at room temperature for 4 hours, the reaction mixture was washed with water, dried over sodium sulfate and evaporated to dryness. The crude product was recrystallized from 1:1 ethyl acetate-hexane to give colorless needles.

B. 2' METHOXYACETYL TAXOL (2'-MAc TAXOL)

A solution containing 100 mg (0.12 mmoles) of taxol 60 mg (0.32 mmoles) of Mac-NHS and 38 milliliters (0.30 mmoles) of diisopropylethylamine in 3 milliliters of dry dichloromethane was refluxed for 3 hours under nitrogen, followed by stirring at room temperature for 18 hours. The reaction was quenched by adding 8 microliters (0.2 mmoles) of methanol. After stirring for 15 minutes, the reaction mixture was washed with 2×3 milliliter portions of 0.1N HCl. The dichloromethane layer was separated and dried over magnesium sulfate. The solvent was then removed by distillation in vacuo at room temperature, to yield 90 mg (82% yield) of product. Purity, determined by HPLC analysis, was greater than 95%. The product was characterized by NMR and FAB-MS (M+H) $^+$926.3, the $^1$H NMR spectrum of the product was similar to that of taxol except for the following major differences δ5.60 (d, 1H), 6.04 (d, 1H).

C. TAXOL-7-PHENYL CARBAMATE 17.5 mg (0.019 mmol) of 2' MAc taxol, 4.5 (0.038 mmol) of phenyl isocyanate, 12 milligram (0.019 mmol) of dibutyltin dilaurate and 2 milliliters of dry methylene chloride were placed in a 10 milliliter round-bottomed flask. The reaction mixture was refluxed for 18 hours. To the cooled reaction mixture was added 5 milliliters of hexane and the precipitated white solid was isolated by centrifugation. The $^1$H NMR spectrum of the product showed the expected multiple for the 7-H at 5.56 ppm. To the crude product was added 1 milliliter of methanol and 10 µL of ethanolamine and the solution was stirred at room temperature for 15 minutes. The reaction mixture was diluted with 5 milliliter of methylene chloride, washed with water, and after the usual work up was purified by preparative HPLC to give 9.8 mg. of the named compound (53%).

EXAMPLE 7

PREPARATION OF TAXOL-7-PHENYLCARBAMATE-2'-mPEG 42,000 ESTER mPEG 42,000 acid, prepared according to example 5A is azeotroped in toluene prior to use and 420 mg (0.01 mmol) is dissolved in 10 ml of anhydrous methylene chloride at room temperature. The above solution is treated with 1,3-diisopropylcarbodiimide (2.28 µl, 0.015 mmol), 4-dimethylaminopyridine (1.83 mg, 0.025 mmol) and taxol-7-phenylcarbamate (14.8 mg, 0.015 mmol) at 0° C. The reaction solution is warmed to room temperature after 30 minutes and kept at that temperature for about 16 hours. The reaction solution is then washed with 0.1N HCl, dried and evaporated to yield a solid which is crystallized from 2-propanol to yield the named product.

EXAMPLE 8

PREPARATION OF PODOPHYLLOTOXIN 4-PEG 40,000 DIESTER

PEG 40,000 diacid prepared in accordance with Example 1A was azeotroped before use. The PEG 40,000 diacid (3 grams, 0.125 mmol) was dissolved in 20 ml of anhydrous methylene chloride at room temperature. The above solution was treated with 1,3-diisopropyl carbodiimide (52.2 ml, 0.342 mmol), 4-dimethylamino pyridine (64.0 mg, 0.523 mmol) and podophyllotoxin (Aldrich Chemicals, Milwaukee, Wis.) (142 mg 0.342 mmol), at 0°. The reaction mixture was warmed to room temperature after 30 minutes and kept at that temperature for 16 hours. The reaction mixture was then washed with 0.1N HCl, dried and evaporated to yield a solid which was crystallized from 2-propanol to yield 2.5 grams, (80% yield).

EXAMPLE 9

IN VITRO BIOASSAY

In this example, a series of in vitro assays were conducted to determine the IC$_{50}$ for unmodified taxol, taxol-7-phenylcarbamate (Example 6) 2'-PEG 5,000-taxol (Example 4b), unmodified camptothecin and 20-camptothecin PEG 5,000 ester (Example 3). The unmodified taxol was obtained from PHYTOPharmaceuticals, Inc. and the unmodified camptothecin was obtained from Sigma Chemical Co.

All five compounds were independently tested against the murine lymphoid neoplasm P388/O (Southern Research Institute, parental line) P388/ADR, (Southern Research Institute-Adriamycin-resistant line). Each cell line was grown in RPMI 1640 medium (Whittaker Bioproducts, Walkersville, Md.) +10% FBS (Hyclone Inc., Logan, Utah). Bioassays were performed using RPMI 164+10% FBS with the addition of antibiotics at the following concentrations: penicillin (100 units/ml), streptomycin (100 µg/ml), Fungizone (0.25 µg/ml), and gentamycin (50 µg/ml). Taxol, taxol-7-phenylcarbamate and camptothecin were dissolved in DMSO and diluted to the appropriate concentration in medium. PEG-taxol and PEG-camptothecin were dissolved in water and diluted to the appropriate concentrations.

The assays were performed in duplicate in 96-well microtiter cell culture plates. After the drug had been appropriately diluted in the microtiter plate, 2×10$^3$ cells were added to each well and the plates were incubated at 37° C. in a humidified incubator with 5% CO$_2$. After 3 days (72 hours), cell growth was measured by the addition of a metabolic indicator dye (either MTT or Alamar Blue) according to standard protocols. The IC$_{50}$ for each test compound was determined then compared to the IC$_{50}$ for the appropriate reference compound. The results are shown below:

| | IC$_{50}$ (nM) | |
|---|---|---|
| | CELL LINE | |
| DRUG | P388/0 | P388/AD |
| taxol | 6 | 120 |
| taxol-7-phenyl-carbamate | 17 | 88 |
| 2'-PEG 5,000 taxol | 15 | 240 |
| camptothecin | 7 | 12 |
| 20-camptothecin-PEG 5,000 | 33 | 44 |

Referring now to the table, it can be seen that the taxol-7-phenyl carbamate, and relatively low molecular weight polymer prodrugs compare favorably to unmodified forms of the drug. Applicants, however, have surprisingly found that results with the polymer prodrugs were not consistent with the results obtained when in vivo tests were undertaken. See Example 10 below.

EXAMPLE 10

IN VIVO STUDY

In this Example, 40 female mice, approximately 8–10 weeks old at the beginning of the experiment, and obtained from Charles River Laboratories, Wilmington, Mass. were broken up into 4 groups of 10. The mice were infected with the P388/0 murine lymphoid neoplasm to determine the in vivo effects of prodrugs prepared in accordance with the present invention. This experiment followed the procedure of Ward, et al. set forth in *Cancer Chemother. Pharmacol.*, 31:255–257 (1992), the contents of which are incorporated by reference herein. The purpose of the study was to determine the ability of the prodrug to increase the life span of the mice.

Each mouse was implanted with $5 \times 10^5$ P388/0 cells on day zero and treated with the respective drug for five consecutive days. Ten mice were injected with vehicle (50/50 Cremophor EL/ethanol) alone and ten mice were untreated (controls). The final endpoint for the example is survival. The resulting data is presented below:

| DRUG | DOSE/ DAY µM | TOTAL DOSE µM | TIME TO 50% SURVIVAL DAYS | MEAN TIME TO DEATH DAYS |
|---|---|---|---|---|
| CONTROL-UNTREATED | 0 | 0 | 12.5 | 12.6 ± 1.2 |
| CONTROL-VEHICLE | 0 | 0 | 12.5 | 12.7 ± 1.3 |
| Taxol | 0.35 | 1.75 | 18 | 18.7 ± 1.3 |
| 2'-PEG 5,000 Taxol | 0.35 | 1.75 | 12.9 | 14.1 ± 2.3 |
| 2'-PEG 40,000 Taxol | 0.35 | 1.75 | 19.0 | 20.3 ± 1.1 |
| Taxol | 1.05 | 5.25 | 7.25 | 7.8 ± 1.40 |
| 2'-PEG 5,000 | 1.05 | 5.25 | 15.0 | 15.7 ± 2.1 |
| 2'-PEG 40,000 Taxol | 1.05 | 5.25 | 5.75 | 6.3 ± 0.5 |
| 20 Campto.-PEG 40,000 | 0.35 | 1.75 | 24.0 | 24.9 |
| 20 Campto.-PEG 40,000 | 0.70 | 3.50 | 10.0 | 29.0 |

The data can be summarized as follows: all compounds increased the life span of the mice versus the controls at doses of 1.75 µmoles/mouse. It was surprisingly found that the 2'-PEG 5,000 was significantly less effective than taxol ($p < 0.001$) at this dosage. Even at triple the dose, the PEG 5,000 prodrug (5.25 µmoles/mouse) was still significantly less effective than the parent compound (taxol at 1.75 µmoles/mouse). On the other hand, the prodrug prepared with PEG 40,000 diacid is approximately equivalent to the parent compound at doses of 1.75 µmoles/mouse, (extended survival due to anti-tumor activity) and doses of 5.25 µmoles/mouse (shortened survival due to toxicity). While Applicants are not bound by theory, it is believed that the unique combination of higher molecular weight polymer to increase the circulating life of the prodrug and the rapid rate of hydrolysis of the particular ester linkage allow therapeutic amounts of the parent compound to be generated before the prodrug is cleared from the body.

Separately, it was observed that the 20-camptothecin-PEG 40,000 substantially increased survival time when compared to the controls.

EXAMPLE 11

T$_{1/2}$ HYDROLYSIS TIME

In this example, the $t_{1/2}$ for hydrolysis of an ester-based prodrug linkage prepared in accordance with the present invention was compared to the ester linkage disclosed in PCT W093/24476. In particular, the 2'- PEG ester of Example 1B was compared to the prodrug designated as compound (7) in the PCT publication except that mPEG 5,000 was used to prepare the PEG acid. The prodrug compositions of Example 1B and the comparative compound described above were thus prepared to have the following substituents in the 2' position:

| | Taxol 2'-substitution |
|---|---|
| Example 1B: | O—C(O)—CH$_2$—O—(CH$_2$—CH$_2$O)$_m$—CH$_2$—C(O)—O |
| Comparative: | O—C(O)—CH$_2$CH$_2$—C(O)O—(CH$_2$—CH$_2$O)$_n$—CH$_3$ | m = 909, such that PEG has a MW of 40,000
n = 114, such that PEG has a MW of 5,000.

The comparative ester-based prodrug was prepared in the following manner:

a. Comparative 2' mPEG-taxol ester synthesis mPEG MW 5,000 succinic acid (SS acid) prepared as reported in the literature (Abuchowski, A., et al., *Cancer Bichem. Biophys.* 7,175–186 (1984), (300 mg, 0.0588 mmol) and taxol (75.3 mg, 0.0882 mmol) were azeotroped with toluene (40 ml) for 2 hours. 20 ml of toluene was removed and the mixture was cooled to room temperature and the solvent was removed under reduced pressure using a rotary evaporator. The residue was dissolved in anhydrous methylene chloride (10 ml) followed by the addition of diisopropylcarbodiimide (11.1 mg, 0.0882 mmol) and dimethyl aminopyridine (10.8 mg, 0.002 mmol). The reaction mixture was stirred at room temperature overnight. The mixture was then washed with 0.1N HCl and the solvent was dried (anhydrous sodium sulfate) and removed by rotary evaporator. The resulting residue was crystallized from 2-propanol to give 252 mg of solid material which was shown to be a mixture of two compounds, the required product and a free PEG component. This mixture was purified by Prep HPLC using a 47 mm ×300 mm C8 cartridge column (Waters PrepPack) under a radial pressure of 600 psi, using methanol water gradient system as the mobile phase. The pure product (40 mgs) was characterized by proton NMR and HPLC.

The rate of hydrolysis for each compound was determined by the following tests:

b. Hydrolysis of bis taxol 2' ester of PEG 40,000 diacid in phosphate buffer pH 7.3

The ester of Example 1B was dissolved in pH 7.3 phosphate buffer at a concentration of 20.3 mg/ml (equivalent to 0.5 mg/ml of taxol based on UV assay) and kept at 37° C. Thereafter, 10 µl samples were withdrawn from the solution at one hour intervals and injected directly into HPLC. The area under the taxol peak was compared with a standard curve generated for taxol (amount vs peak area). Accordingly, the amount of taxol formed by hydrolysis was calculated. In this case, the half life of the prodrug, i.e., the time taken for 50% of prodrug to hydrolyze was found to be 5–6 hours.

c. Hydrolysis of bis taxol 2' ester of PEG 40,000 diacid in rat plasma

The ester of Example 1 was dissolved in rat plasma, physiological pH: approximately 7.3 (with unspecified esterase activity) at a concentration of 6 mg/ml (equivalent to 0.15 mg/ml of taxol based on UV assay) and kept at 37° C. Thereafter, 100 µl portions were withdrawn at regular intervals and extracted with 3×500 µl of ethyl acetate. The organic layers were combined and evaporated to dryness. The residue was dissolved in 50 µl of methanol and injected into a HPLC. The area under the taxol peak was compared to the standard curve generated for taxol and the amount of taxol formed by hydrolysis was calculated. In this case, the half life was determined to be 1.6 hours, indicating that substantial esterase activity was present.

d. Hydrolysis of bis taxol 2' ester of PEG 40,000 diacid in distilled water

The procedure of Example 11c. was repeated except that distilled water was used in place of rat plasma. The half life for the product of Example 1 was determined to be greater than 96 hours.

e. Hydrolysis of comparative 2' mPEG taxol esters

The procedures of steps b, c and d were repeated using the comparative taxol prodrug produced in step a. The results are set forth below:

| | $T_{12}$ HYDROLYSIS (HRS) | | |
|---|---|---|---|
| PRODRUG | PBS BUFFER (pH 7.3) | RAT PLASMA (pH 7.3) | DISTILLED WATER (pH 6.8) |
| EXAMPLE 1 | 5.0 | 1.6 | >96 |
| COMPARATIVE | >96 | >7 | >96 |

As can be seen from the table, the prodrug formulations of the present invention have substantially quicker rates of hydrolysis than that shown in the prior art. In distilled water, pH 6.8, it can be seen that both compounds are essentially stable. The rate enhancement is evident and useful for in vivo environments where esterases are present or not. This relatively rapid regeneration of the parent compound affords benefits which are apparent only after conducting in vivo analyses of PAO prodrug compounds.

As was demonstrated in Example 9, the results of the in vitro tests suggest that hydrolysis of the polymer linkage was sufficient to effect cytotoxicity. The in vivo tests of Example 10, however, clearly show that regeneration of sufficient amounts of the parent compound during the time the prodrug remains in circulation is a key to providing an effective prodrug composition.

Thus, ester linkages with relatively long $t_{1/2}$ hydrolysis fail to provide useful PAO-based prodrugs because most of the parent compound is excreted before being released in vivo. This effect is especially apparent when relatively low molecular weight polymers are used.

EXAMPLE 12

PREPARATION OF TAXOL 2'-PEG 40,000 DIAMINE ESTER

PEG 40,000 diamine 20.0 grams, (0.5 mmol) prepared by the procedure of Buckmann, et al., Biotechnology and App.Biochem. (9), 258–268, (1987), the disclosure of which is incorporated herein by reference, is dissolved in methylene chloride (100 ml ) followed by the addition of succinic anhydride (62.5 mg, 0.625 mmol). The mixture is stirred for 5 hours and thereafter the solvent is removed by rotary evaporator. The solid obtained is recrystallized from 2-propanol to give 17 g (84%) of the bis-PEG 40,000 NH—CO—CH₂CH₂COOH.

The PEG 40,000 acid from above is azeotroped in toluene prior to use and 3 grams is dissolved in 20 ml of anhydrous methylene chloride at room temperature followed by the addition of taxol (291.5 mg, 0.342 m.mol), 1,3, diisopropylcarbodiimide (52.2 µl 0.342 m.mol), dimethylaminopyridine (64 mg, 0.523 mmol), at 0° C. The reaction solution is warmed to room temperature after 30 minutes and kept at that temperature for 16 hrs. The reaction solution is then washed with 0.1N HCl, dried and evaporated to yield a white solid which is crystallized from 2- propanol to give about 2.5 grams of the named product.

We claim:

1. A composition of the formula:

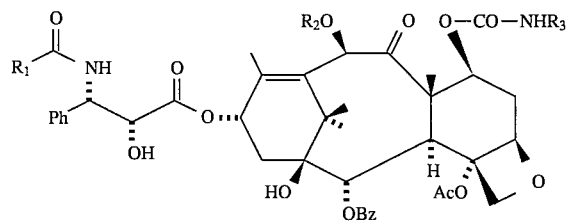

wherein:

$R_1$ is $C_6H_5$ or $(CH_3)_3CO$;

$R_2$ is H or $CH_3CO$; and $R_3$ is aryl, aralkyl or heteroaryl.

2. The composition of claim 1, wherein $R_3$ is phenyl.

3. A taxane-based composition, comprising the formula:

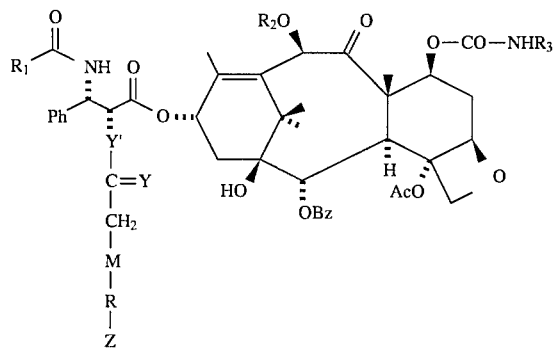

wherein:
- $R_1$ is $C_6H_5$ $(CH_3)_3CO$;
- $R_2$ is H or $CH_3CO$;
- $R_3$ is aryl, aralkyl or heteroaryl;
- M is X or Q;
- X is an electron withdrawing group;
- Q is a moiety containing a free electron pair positioned five or six atoms from Y',
- Y and Y' are independently O or S;
- R is a polyalkylene oxide; and
- Z is one of OH, a $C_{1-4}$ alkyl moiety or

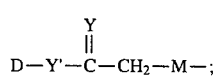

wherein
- D is a biologically active nucleophile.

4. The composition of claim 3, wherein R is a polyethylene glycol.

5. The composition of claim 3, wherein X, Y and Y' are each O.

6. The composition of claim 3, wherein Z is methyl.

7. The composition of claim 3 comprising the structure:

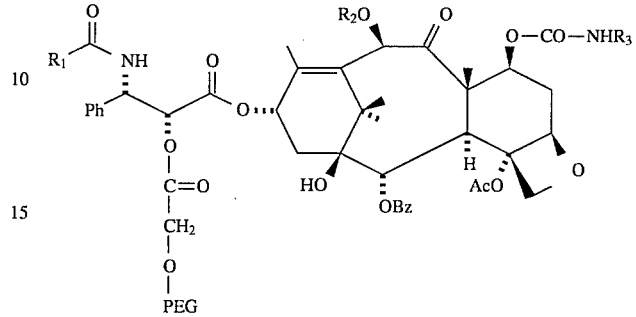

wherein:
- $R_1$ is $C_6H_5$ or $(CH_3)_3CO$;
- $R_2$ is H or $CH_3CO$; and
- $R_3$ is aryl, aralkyl or heteroaryl.

8. The composition of claim 3, wherein said polyalkylene oxide has a molecular weight of from about 20,000 to about 80,000.

9. The composition of claim 8, wherein said polyalkylene oxide has a molecular weight of from about 25,000 to about 45,000.

10. The composition of claim 9, wherein said polyalkylene oxide has a molecular weight of from about 30,000 to about 42,000.

* * * * *